US009101496B2

(12) United States Patent
Phipps

(10) Patent No.: US 9,101,496 B2
(45) Date of Patent: Aug. 11, 2015

(54) ULTRASONIC ORTHOPEDIC TAPER DISSOCIATION DEVICE AND METHOD

(71) Applicant: Zimmer, Inc., Warsaw, IN (US)

(72) Inventor: James P. Phipps, South Whitley, IN (US)

(73) Assignee: Zimmer, Inc., Warsaw, IN (US)

( * ) Notice: Subject to any disclaimer, the term of this patent is extended or adjusted under 35 U.S.C. 154(b) by 287 days.

(21) Appl. No.: 13/689,062

(22) Filed: Nov. 29, 2012

(65) Prior Publication Data

US 2013/0138163 A1    May 30, 2013

Related U.S. Application Data

(60) Provisional application No. 61/565,083, filed on Nov. 30, 2011.

(51) Int. Cl.
*A61F 2/46* (2006.01)
*A61N 7/00* (2006.01)

(52) U.S. Cl.
CPC ............... *A61F 2/4637* (2013.01); *A61N 7/00* (2013.01); *A61F 2002/4641* (2013.01); *A61F 2002/4683* (2013.01)

(58) Field of Classification Search
CPC ..... A61B 17/8847; A61N 7/00; A61F 2/4607
USPC .......................................................... 606/99
See application file for complete search history.

(56) References Cited

U.S. PATENT DOCUMENTS

| | | | |
|---|---|---|---|
| 4,787,907 A | 11/1988 | Carignan | |
| 5,019,083 A | 5/1991 | Klapper et al. | |
| 5,045,054 A * | 9/1991 | Hood et al. | 604/22 |
| 5,080,679 A | 1/1992 | Pratt et al. | |
| 5,318,570 A | 6/1994 | Hood et al. | |
| 5,405,404 A | 4/1995 | Gardner et al. | |
| 5,733,285 A | 3/1998 | Errico et al. | |
| 5,885,301 A * | 3/1999 | Young | 606/99 |
| 6,132,469 A | 10/2000 | Schroeder | |
| 6,669,728 B2 | 12/2003 | Despres, III et al. | |
| 6,786,931 B2 | 9/2004 | Hazebrouck | |
| 7,323,013 B2 | 1/2008 | McTighe et al. | |
| 7,867,282 B2 | 1/2011 | Heck et al. | |

FOREIGN PATENT DOCUMENTS

| | | | |
|---|---|---|---|
| EP | 2055274 B1 | 10/2010 | |
| EP | 2055273 B1 | 12/2010 | |

* cited by examiner

*Primary Examiner* — Andrew Yang
(74) *Attorney, Agent, or Firm* — Schwegman Lundberg & Woessner, P.A.

(57) ABSTRACT

A dissociation device comprises a transducer configured to produce acoustic vibration selected to be sufficient to dissociate a male portion from an engaged female portion of a medical device, a power source configured to supply power to the transducer, and a processor for controlling the transducer. The transducer can be configured to produce ultrasonic acoustic vibration. The male portion of the medical device can comprise a male taper and the female portion can comprise a corresponding female taper.

19 Claims, 14 Drawing Sheets

ULTRASONIC ORTHOPEDIC TAPER DISSOCIATION DEVICE AND METHOD

CROSS-REFERENCE TO RELATED APPLICATION

This application claims the benefit of. U.S. Provisional Application No. 61/565,083, filed Nov. 30, 2011, which is herein incorporated by reference.

BACKGROUND

Medical implants, such as orthopedic implants, often use tapers for connecting components. A taper junction typically includes a male taper portion that fits within and engages a female taper portion. Often, a taper may need to be dissociated or disengaged after the male taper portion has been engaged with the female taper portion. However, due to the strong holding strength of tapers, disengagement of tapers can be difficult and often requires applying a large force to the implant, such as a large impact, rotational, or pulling force on the components in an attempt to disengage the taper. Taper dissociation may be difficult for a surgeon or other medical practitioner to achieve due to the large dissociation forces required.

SUMMARY

The present disclosure relates generally to a device and method for dissociating a taper of a medical device, such as a taper used for connecting components of an orthopedic implant. The device or method can include applying to the taper acoustic vibration, such as ultrasonic vibration, that is sufficient to dissociate a male portion of the taper from a female portion of the taper.

In an example, the present disclosure is directed to a dissociation device comprising a transducer configured to produce acoustic vibration selected to be sufficient to dissociate a male portion from an engaged female portion of a medical device.

In an example, the present disclosure is directed to a method comprising providing or obtaining access to a medical device comprising a first component comprising a male portion and a second component comprising a corresponding female portion engaged with the male portion, and applying acoustic vibration to the medical device, wherein the acoustic vibration is configured to dissociate the male portion from the female portion.

In an example, the present disclosure is directed to a dissociation device comprising an ultrasonic transducer configured to produce ultrasonic vibration selected to be sufficient to dissociate a male taper portion from an engaged corresponding female taper portion of a medical device, wherein a first component of the medical device comprises the male taper portion and a second component of the medical device comprises the female taper portion, wherein the transducer is configured to produce the ultrasonic vibration with a frequency that is within a predetermined or specified threshold of a natural frequency of vibration of at least one of the medical device, the first component, the second component, the male taper portion, or the female taper portion. The dissociation device also comprises a processor configured to control the ultrasonic transducer, a memory configured to store at least one of the natural frequency of vibration, the predetermined or specified threshold, and one or more instructions for the processor, and a user interface configured to allow a user to select a frequency for the ultrasonic vibration.

This summary is intended to provide an overview of subject matter of the present disclosure. It is not intended to provide an exclusive or exhaustive explanation of the disclosure. The detailed description is included to provide further information about the present disclosure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure relates generally to a device and method for dissociating a taper of a medical device, such as a taper use for connecting components of an orthopedic prosthetic implant. The device or method can include applying ultrasonic or other acoustic vibration to the taper that is sufficient to dissociate a male portion of the taper from a female portion of the taper. The use of ultrasonic or other acoustic vibration to disengage the male taper portion from the female taper portion allows the taper to be dissociated without requiring resorting to the exertion of large physical forces on the medical device or the patient.

Figure 1:
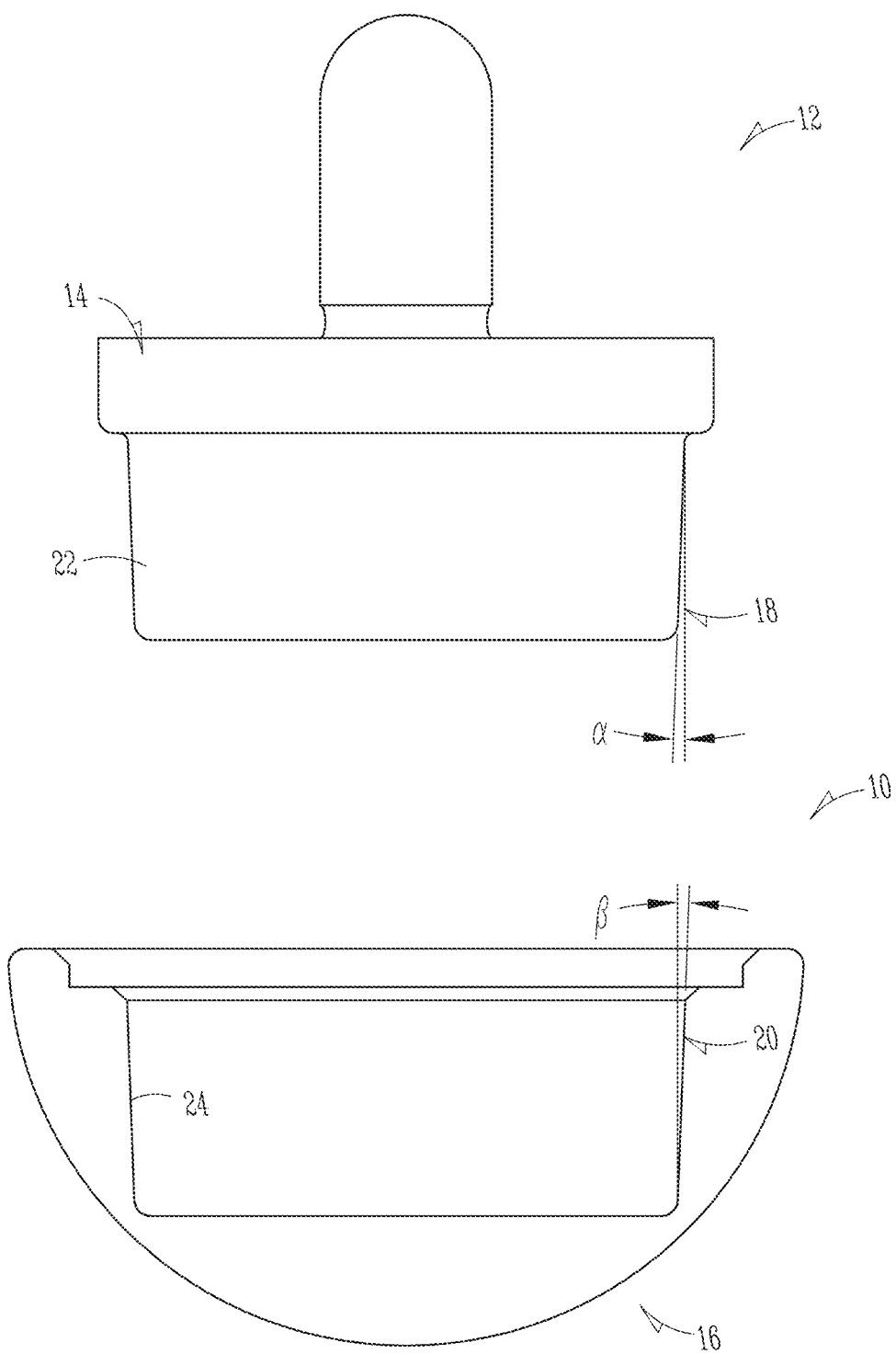
FIG. 1 is a schematic diagram showing an example of a first component of a medical device having a male taper portion and a second component of the medical device having a female taper portion.
Figure 2:
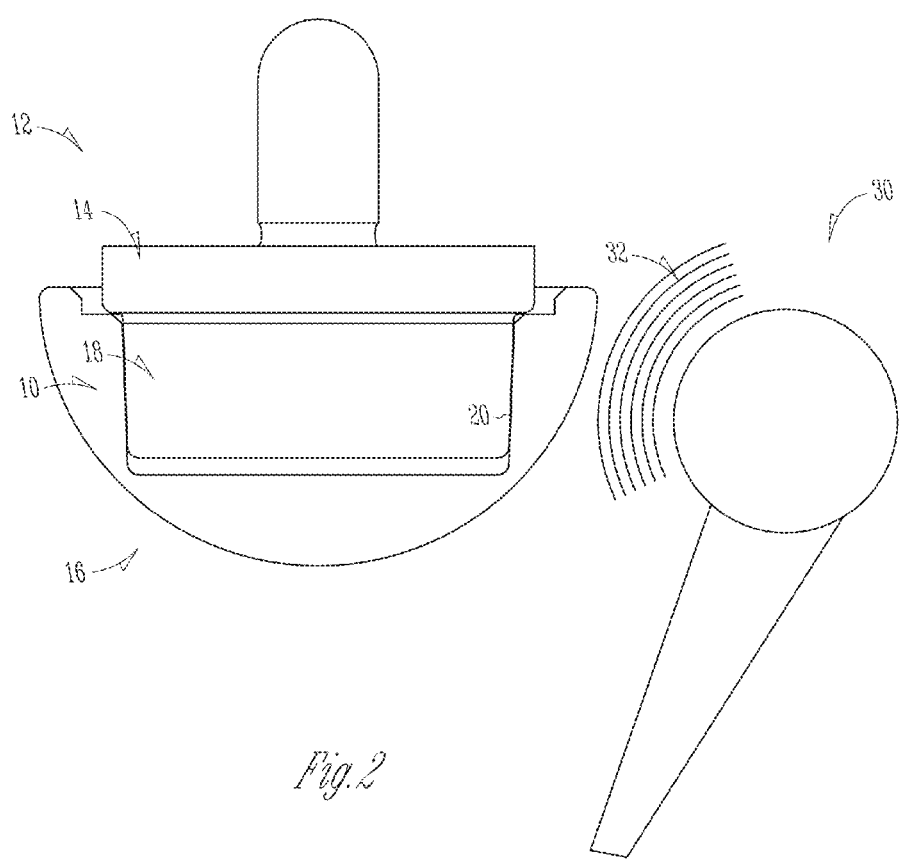
FIG. 2 is a schematic diagram of an example of the medical device of FIG. 1 with the male taper portion of the first component engaged with the female taper portion of the second component.

FIGS. 1 and 2 show a generic example of a taper 10 that can be used in a medical device, shown as a generic medical device 12 in FIGS. 1 and 2, such as to couple a first component 14 to a second component 16. First component 14 can comprise a male taper portion 18 while second component 16 can comprise a female taper portion 20 that can engage with male taper portion 18 so as to couple first component 14 to second component 16, such as shown in FIG. 2. In an example, male taper portion 18 can comprise an external tapered surface 22 while female taper portion 20 can comprise a corresponding mating internal tapered surface 24. In an example, external tapered surface 22 can include a generally frustoconical surface that angles inwardly from a radial exterior of first portion 14 at an angle α. In the same example, internal tapered surface 24 can also include a generally frustoconical surface that angles outwardly from a radial interior of second portion 16 at an angle β. Angle α is substantially equal to angle β such that when male taper portion 18 is engaged within female taper portion 20, external tapered surface 22 of male taper portion 18 is substantially abutted against internal tapered surface 24 of female taper portion 20 so as to provide sufficient frictional force to retain first component 14 and second component 16 together in a manner that is capable of withstanding the typical forces that are exerted onto medical device 12 when it is implanted into a patient.

FIG. 1 shows first component 14 and second component 16 separated such that male taper portion 18 is not engaged with female taper portion 20. In an example, such as during assembly or implantation of medical device 12, male taper portion 18 can be engaged with female taper portion 20, e.g., by inserting male taper portion 18 into female taper portion 20 so that external tapered surface 22 of male taper portion 18 engages internal tapered surface 24 of female taper portion 20, for example by being abutted against internal tapered surface 24 so as to provide the frictional force described above. FIG. 2 shows an example of male taper portion 18 engaged with female taper portion 20. Once male taper portion 18 is engaged with female taper portion 20, first component 14 will remain coupled with second component 16 until male taper portion 18 is dissociated from female taper portion 20.

Figure 3:
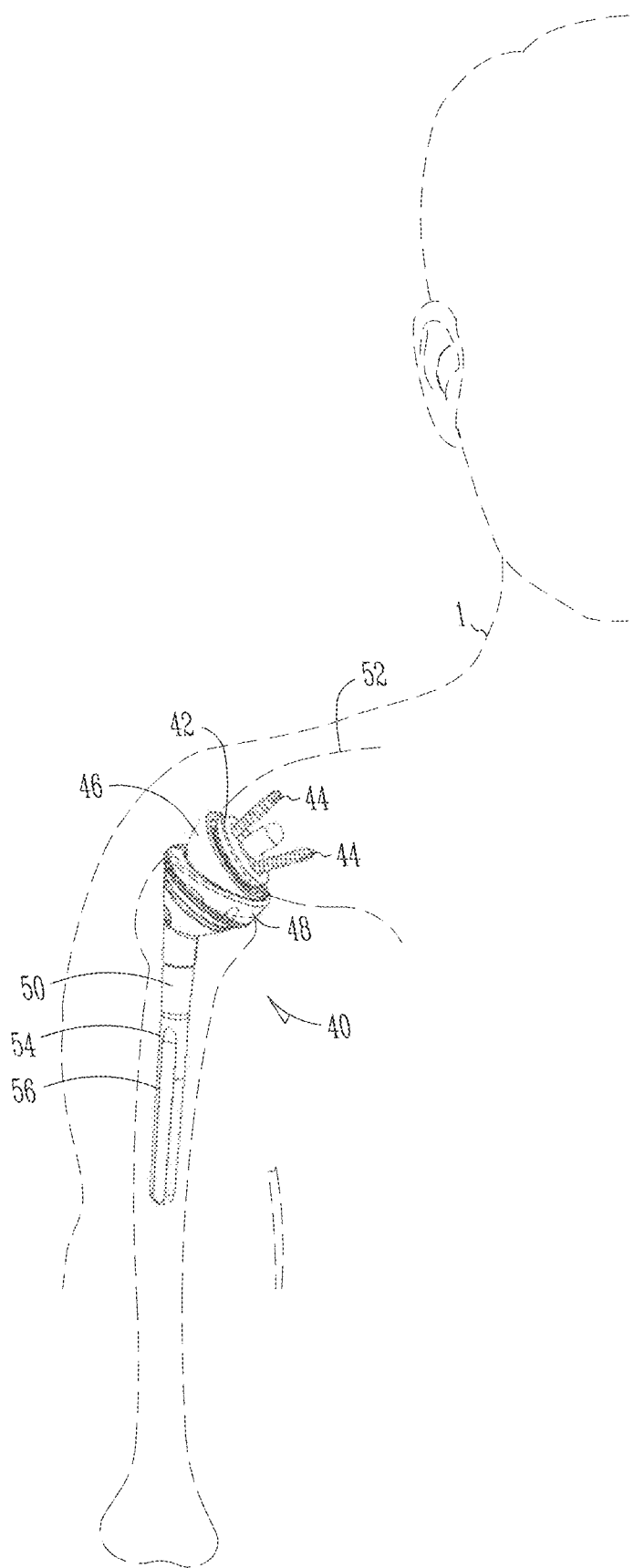
FIG. 3 is a conceptual view of an example of an artificial shoulder implanted in a patient, the artificial shoulder comprising a taper connection between a base plate and a glenosphere.
Figure 4:
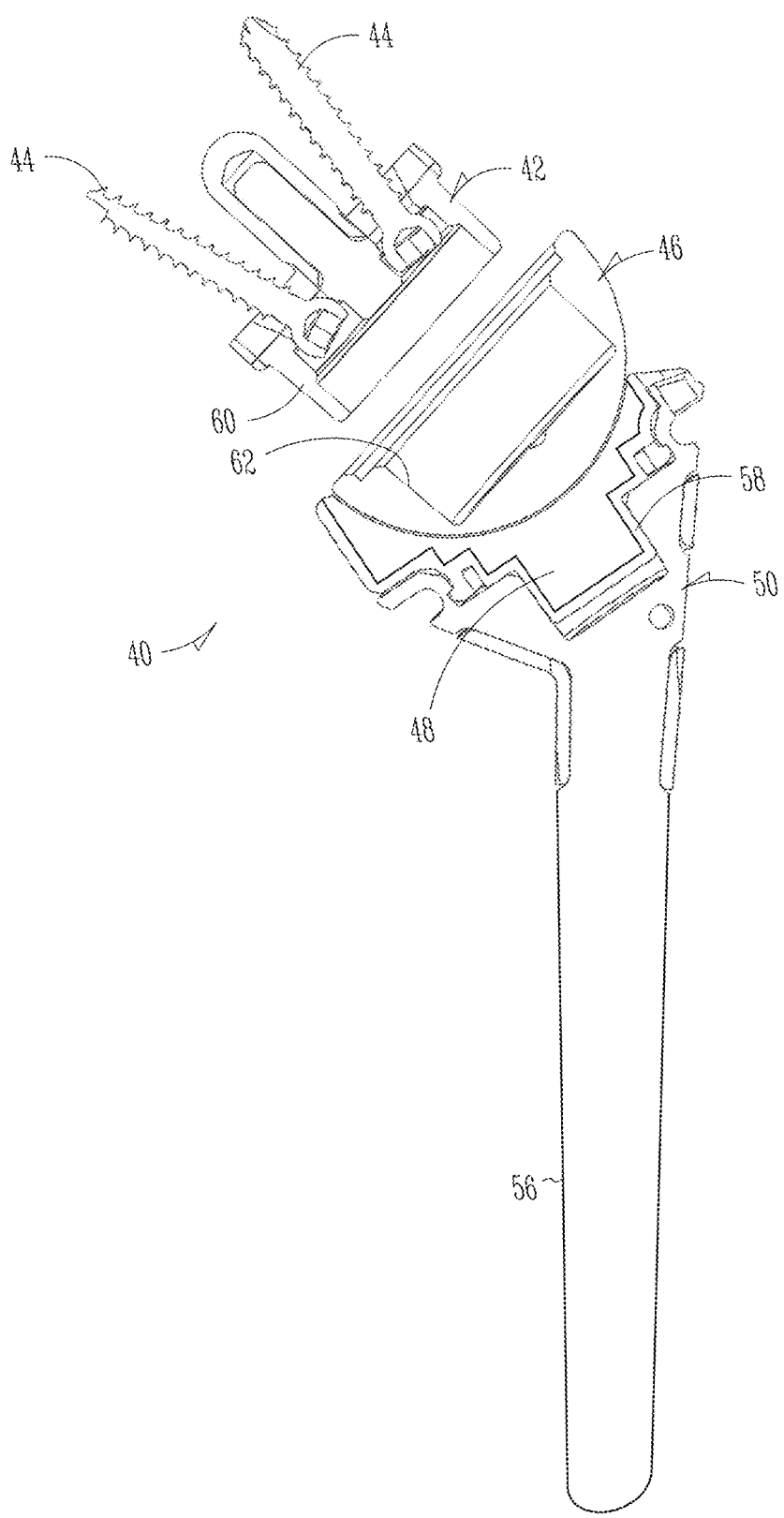
FIG. 4 is exploded view of an example of the artificial shoulder of FIG. 3.

FIGS. 1 and 2 show medical device 12, first component 14, and second component 16 without any specific structures. Medical device 12 can comprise any device in which a taper can be used to couple one component of the device (e.g., first component 14) to another component of the device (e.g., second component 16). For example, medical device 12 may comprise an implantable orthopedic device, also referred to herein as an orthopedic implant, such as an artificial shoulder implant, an artificial hip implant, an artificial elbow implant, an artificial knee, an artificial ankle implant, an artificial wrist implant, a dental implant, a spinal implant, one or more implants for chronic wear, or one or more implants for trauma or other applications. For example, FIGS. 3 and 4 show an example of an artificial shoulder implant 40 that can include a taper such as for coupling a first component of the shoulder implant with a second component of the shoulder implant. However, the present disclosure is not limited to artificial shoulders, or to any other particular kind of orthopedic implant or prosthetic or other medical device. Rather, the concepts or examples of the present disclosure may be applied to any device that includes a taper, such as to couple a first component to a second component.

After first component 14 has been coupled to, or otherwise associated with, second component 16 by engaging male taper portion 18 with female taper portion 20, it may be desirable to decouple first component 14 from second component 16, e.g., by disengaging male taper portion 18 from female taper portion 20. For example, it can be discovered, either post or intra-operatively, that first component 14 is improperly aligned with second component 16 or with another component of medical device 12 or that second component 16 is improperly aligned with first component 14 or another component of medical device 12.

Turning back to FIG. 2, if it is desirable to decouple first component 14 from second component 16, a dissociation device 30 can be used to dissociate male taper portion 18 from female taper portion 20. Dissociation device 30 can produce acoustic vibration 32 configured to dissociate male taper portion 18 from female taper portion 20, such as by exciting a natural frequency of vibration within at least one of male taper portion 18, female taper portion 20, first component 14, second component 16, or medical device 12. This natural frequency of vibration can cause male taper portion 18 to dissociate from female taper portion 20, which is described in more detail below.

Acoustic vibration 32 can be configured to dissociate male taper portion 18 from female taper portion 20, such as by exciting vibration within at least one of male taper portion 18, female taper portion 20, first component 14, second component 16, or medical device 12. In an example, acoustic vibration 32 comprises vibration having an ultrasonic frequency such that acoustic vibration 32 will be referred to herein as ultrasonic vibration 32. Vibration 32 is not limited to ultrasonic vibration, however, and other acoustic frequencies may be used so long as they are sufficient to dissociate a male portion 18 from an engaged corresponding female portion 20.

In an example, ultrasonic vibration 32 is configured with a frequency that is capable of dissociating male taper portion 18 from female taper portion 20 such that the first component becomes disengaged with the second component. In an example, the frequency of ultrasonic vibration 32 can be close to (e.g., substantially the same as, or within a predetermined or specified threshold or range of) a natural frequency of vibration, which can also be referred to as a resonance frequency or resonant frequency, associated with a mode of oscillation relating to at least one of male taper portion 18, female taper portion 20, first component 14, second component 16, or medical device 12.

The threshold or range can comprise a specific frequency of ultrasonic vibration 32, such as can include or range from a particular natural frequency of vibration or within a predetermined or specified percentage or amount from a particular natural frequency of vibration. In an example, the threshold can be a specific frequency range, such as within about 5000 Hz from the natural frequency of vibration, for example within about 1000 Hz from the natural frequency of vibration, such as within about 500 Hz of the natural frequency of vibration. In an example, the threshold can be a particular percentage of the natural frequency of vibration, such as within about 10% of the natural frequency of vibration from the natural frequency of vibration, for example within about 5% of the natural frequency of vibration from the natural frequency of vibration, such as within about 1% of the natural frequency of vibration from the natural frequency of vibration, for example within about 0.1% of the natural frequency of vibration from the natural frequency of vibration. For example, if a natural frequency of vibration of first component 14 and male taper portion 18 is about 7,500,000 Hz (about 7.5 MHz), than a frequency of ultrasonic vibration 32 can be selected to be within about 1000 Hz (about 1 KHz) from the 7.5 MHz natural frequency of vibration, e.g., from about 7,499,000 Hz to about 7,501,000 Hz (from about 7.499 MHz to about 7.501 MHz). The frequency of ultrasonic vibration 32 can, for example, be selected to be within about 5% of the 7.5 MHz natural mode of vibration, e.g., from about 7,125,000 Hz (about 7.125 MHz, or about 95% of the 7.5 MHz natural mode of vibration) to about 7,875,000 Hz (about 7.875 MHz, or about 105% of the 7.5 MHz natural mode of vibration). The values given above are provided simply as an example, and are not meant to limit the scope of the present disclosure.

Without being bound by any particular theory, it is believed that applying ultrasonic vibrations 32 having a frequency that substantially matches a natural frequency of vibration of one or more of the components of medical device 12, e.g., is within the threshold from the natural frequency of vibration, will provide for disengagement of or counteract the frictional forces between male taper portion 18 and female taper portion 20. However, frequencies that do not substantially approach or match a natural frequency of vibration of at least one of male taper portion 18, female taper portion 20, first component 14, second component 16, or medical device 12, e.g., that are outside of the threshold, may also be capable of disengaging or dissociating male taper portion 18 from female taper portion 20. For example, while a particular frequency of ultrasonic vibration 32 may not excite a natural mode of vibration (as described below), it may still excite vibrations within male taper portion 18 or female taper portion 20 that are sufficient to cause dissociation of male taper portion 18 and female taper portion 20.

As noted above, FIGS. 3 and 4 show a specific example of a taper within an orthopedic implant device, in this case an artificial shoulder implant 40. In an example, shown in FIG. 3, artificial shoulder 40 comprises a base plate 42, a glenosphere 46, a liner 48, and a stem 50. In the example shown in FIGS. 3 and 4, when artificial shoulder 40 is implanted in a patient 1, base plate 42 can be attached to the scapula 52 of patient 1, for example by using one or more fasteners (e.g., screws 44), which can be inserted through guide holes in base plate 42 (not shown). Stem 50 can be attached to the humerus 54 of patient 1, for example by inserting a shaft 56 of stem 50 into the medullary cavity of humerus 54 and attaching shaft 56 therein, such as with bone cement or some other attachment means.

In the example shown in FIGS. 3 and 4, glenosphere 46 can be coupled to base plate 42, liner 48 can be coupled to stem 50, and an artificial joint can be formed between the generally hemispherically-shaped glenosphere 46 and a corresponding generally hemispherically-shaped interior surface of liner 48. Artificial shoulder 40 can also include a spacer 58, such as between stem 50 and liner 48. Spacer 58 can be included to help ensure the proper positioning of liner 48 or stem 50 with respect to glenosphere 46 or with respect to scapula 52.

The joint of artificial shoulder 40 can include a ball substitute, e.g., glenosphere 46, that can be coupled to scapula 52, and artificial shoulder 40 can include a socket substitute, e.g., liner 48 and stem 50, that can be coupled to humerus 54. In this way, the joint in the artificial shoulder 40 shown in FIGS. 3 and 4 can be conceptualized as the opposite of the anatomical shoulder joint, which comprises a ball-shaped head on humerus 54 that fits within a socket (the glenoid cavity) within scapula 52. For this reason, artificial shoulder implants comprising a configuration such as that shown in the example of FIGS. 3 and 4 are often referred to as a "reverse" artificial shoulder. The concepts or examples of the present disclosure are not limited to a "reverse" arrangement, but rather can be used for an artificial implant that corresponds to the anatomical arrangement.

In an example, such as shown in FIGS. 3 and 4, base plate 42 can be coupled to glenosphere 46 using a taper coupling formed between a male taper portion 60 on base plate 42 and a female taper portion 62 on glenosphere 46. The present disclosure is not limited to a male taper being located on base plate 42 and female taper located on glenosphere 46. Rather, the type of tapers on each component can be reversed, with a male taper being located on the glenosphere and a female taper located on the base plate. As discussed above with respect to FIG. 1 regarding male taper portion 18 of first component 14 and female taper portion 20 of second component 16, base plate 42 can be coupled to glenosphere 46 by male taper portion 60 being inserted into and engaging with female taper portion 62.

Once male taper portion 60 has engaged female taper portion 62, base plate 42 will remain coupled to glenosphere 46 until the taper connection is disengaged by dissociating male taper portion 60 from female taper portion 62. Dissociation of male taper portion 60 from female taper portion 62 may be desired, for example, after determining that base plate 42 and glenosphere 46 are not properly aligned with each other, or after determining that base plate 42 is not properly aligned in scapula 52 (such as because, in the example shown in FIGS. 3 and 4, glenosphere 46 blocks access to screws 44), or simply to remove artificial shoulder 40, e.g., to replace artificial shoulder 40 with a new artificial shoulder implant. Typically, dissociation of a taper coupling has required the application of a physical force, usually a large physical force such as a large tensile force, to pull glenosphere 46 and base plate 42 apart or a large rotational or torsional force to disengage male taper portion 60 from female taper portion 62. The present disclosure can use ultrasonic or other acoustic energy in the form of ultrasonic vibration 32 that is configured to dissociate or help dissociate male taper portion 60 from female taper portion 62. In instances where ultrasonic or other acoustic energy is used to help dissociate a male taper portion from a female taper portion, one skilled in the art will recognize that those instruments currently used to perform this function can also be used in conjunction with the ultrasonic or other acoustic energy. In one embodiment, ultrasonic or other acoustic energy can initially be used to loosen the taper connection between a first component and a second component, while a standard dissociation tool as known in the art can subsequently be used to completely disassociate these components from one another.

In an example, ultrasonic vibrations 32 can act to excite at least one of male taper portion 60, female taper portion 62, base plate 42, glenosphere 46, or substantially the entirety of artificial shoulder 40 so as to form oscillating vibrations at male taper portion 60 and/or female taper portion 62. It is believed that these oscillating vibrations within male taper portion 60 and/or female taper portion 62 can act to interrupt the frictional forces that are exerted between and hold together the tapered surfaces of male taper portion 60 and female taper portion 62.

In an example, ultrasonic vibration 32 can act to excite a natural frequency of vibration, sometimes also referred to as a resonance frequency or resonant frequency, within at least one of male taper portion 60, female taper portion 62, base plate 42, glenosphere 46, or artificial shoulder 40. The natural frequency of vibration represents a frequency that corresponds to vibrations within at least one particular component, e.g., within base plate 42 or glenosphere 46, forming a repeating geometric shape. FIGS. 5A-5D and 6A-6D show several example mode shapes of natural frequencies of vibration, or modes, of base plate 42 at various frequencies of ultrasonic vibration 32, with FIGS. 5A-5D showing perspective views and FIGS. 6A-6D showing plan views of base plate 42. FIGS. 7A-7D and 8A-8D show several example mode shapes of natural frequencies of vibration, or modes, of glenosphere 46 at various frequencies of ultrasonic vibration 32, with FIGS. 7A-7D showing perspective views and FIGS. 8A-8D showing plan views of glenosphere 46. The "mode," "resonant frequency mode," or "natural frequency mode," can represent one of a plurality of natural frequencies of vibration that a particular component may experience. The "order" can represent the specific one of the plurality of modes that is experienced. For example, a "first order mode" can represent a first or lowest natural frequency of vibration, a "second order mode" can represent the second or next highest natural frequency of vibration, and so on. The mode shapes that are shown in the figures and described herein illustrate examples of mode shapes that are believed to permit efficient dissociation of the taper junctions. These "mode shapes" shown in the figures can also be referred to herein as "desired mode shapes." However, other mode shapes of vibration can be useful in dissociating a taper junction, and the present disclosure is not limited to the resonant mode shapes shown or described with respect to FIGS. 5 and 6.

Figure 5A:
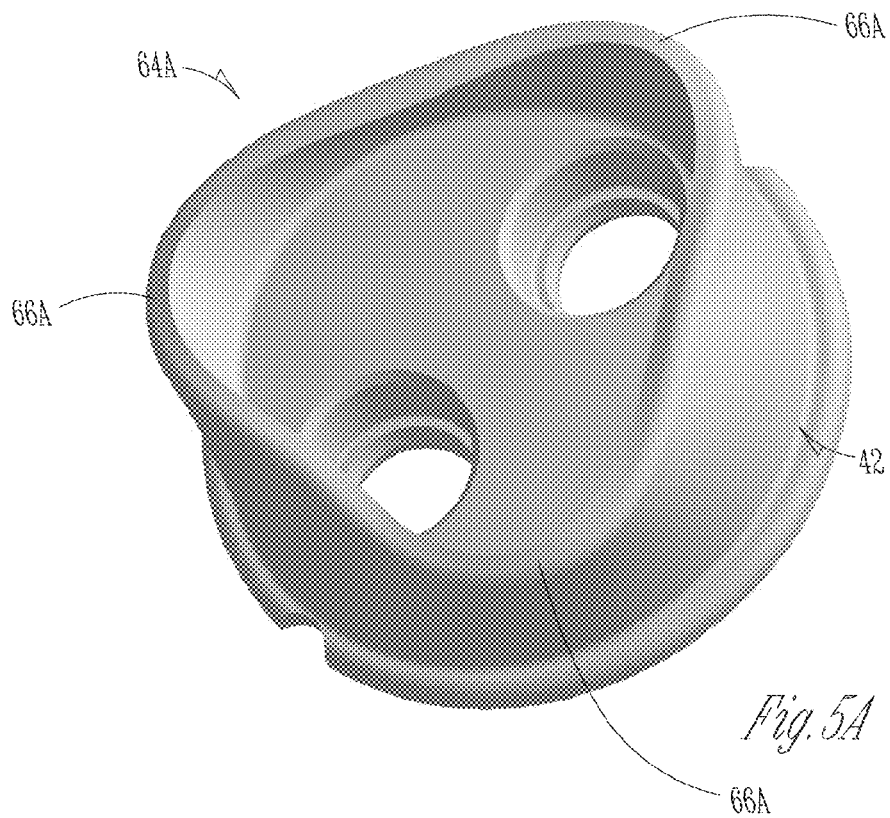
FIGS. 5A-5D are perspective views of examples of mode shapes at natural frequencies of vibration of the base plate of the artificial shoulder of FIG. 3 when the base plate is subjected to ultrasonic vibration configured to dissociate the taper connection between the base plate and the glenosphere.
Figure 6A:
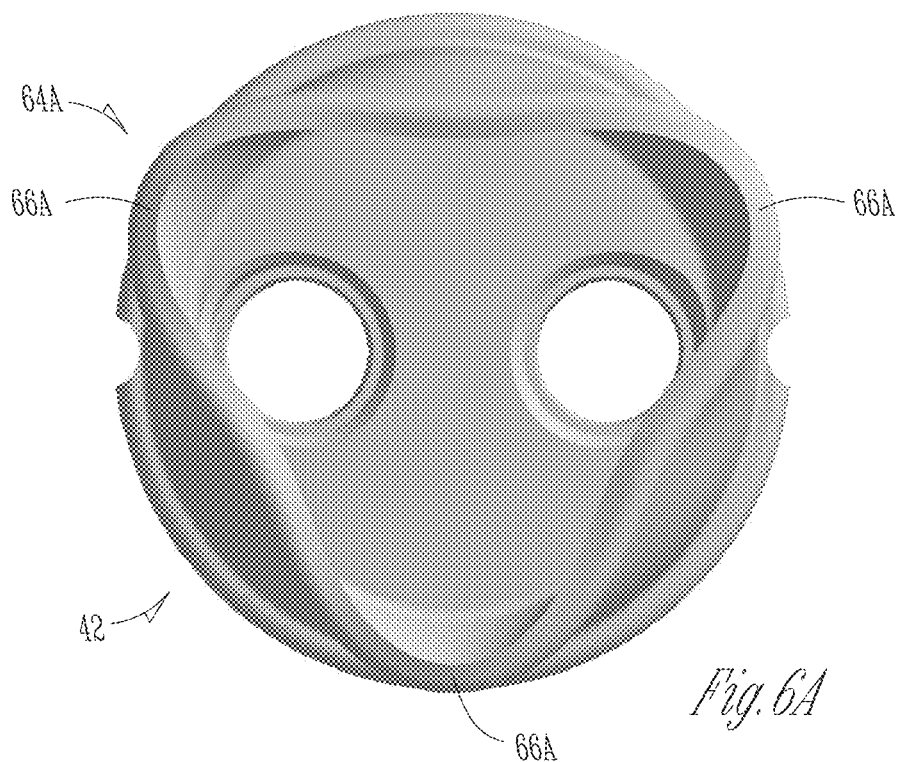
FIGS. 6A-6D are plan views of examples of the mode shapes at natural frequencies of vibration of the base plate shown in FIGS. 5A-5D.
Figure 6B:
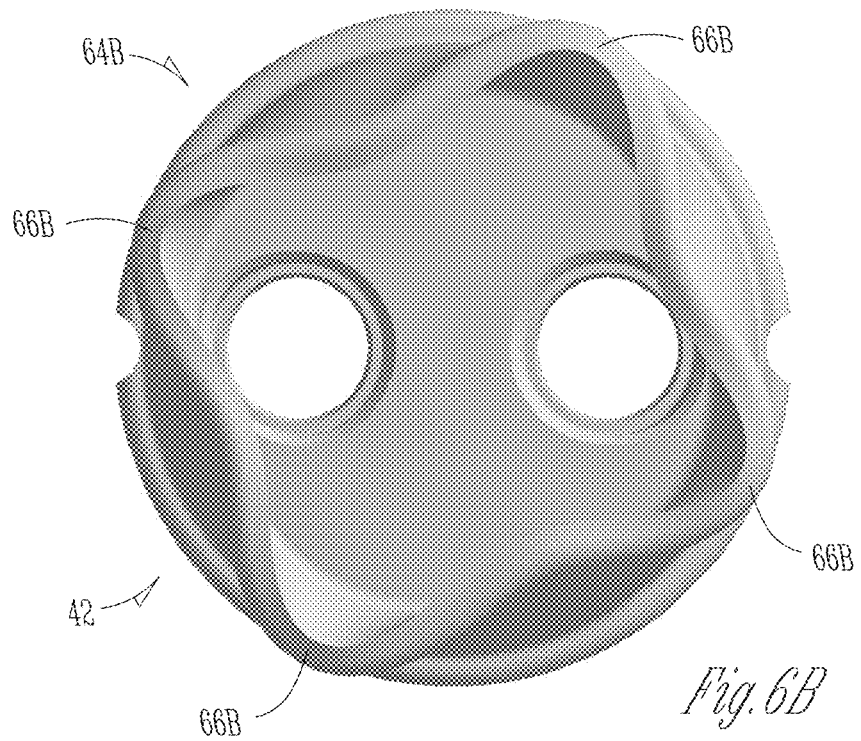
Figure 6C:
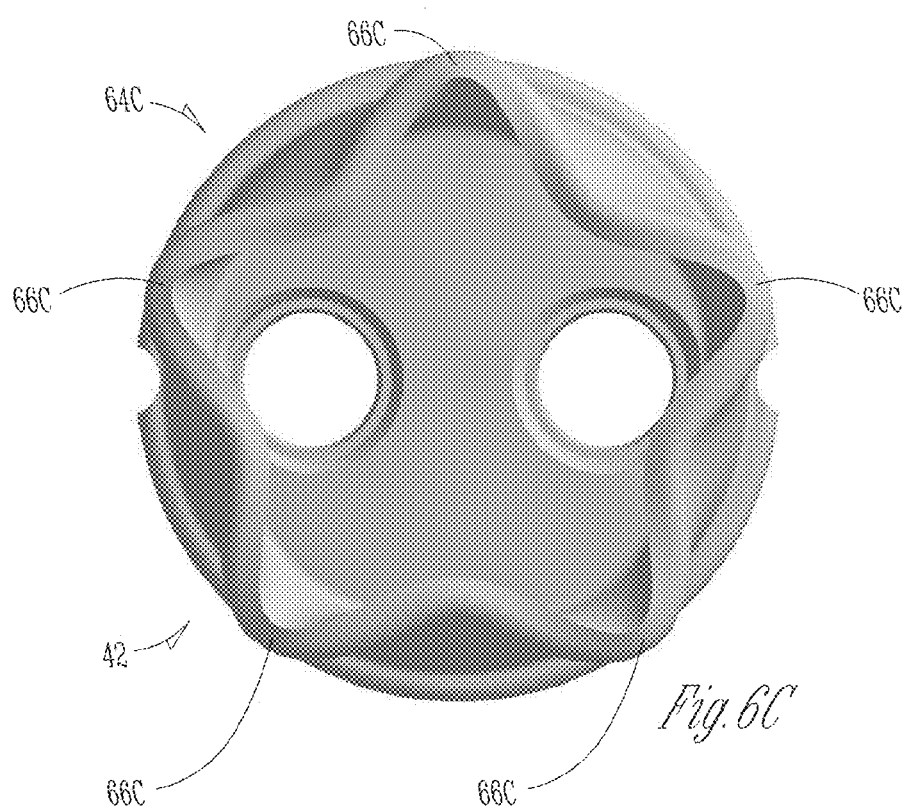
Figure 6D:
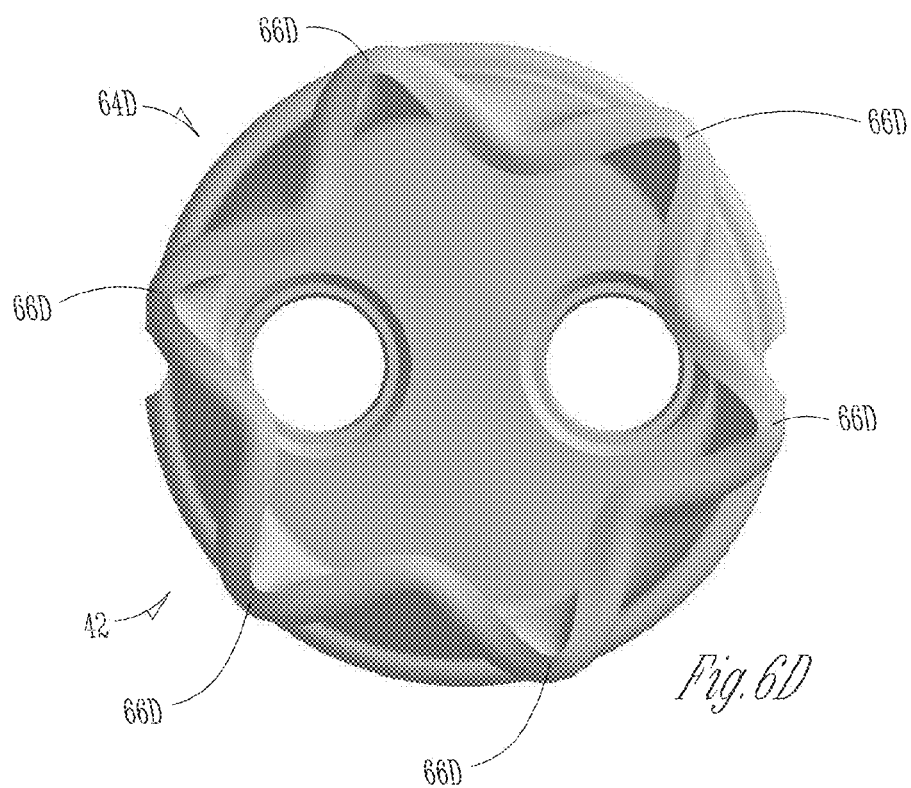

FIGS. 5A and 6A shows base plate 42 within a first order mode while being exposed to a first frequency of ultrasonic vibration 32 that substantially matches a first natural frequency of vibration of base plate 42 such that base plate 42 comprises a first resonant frequency mode shape 64A. As shown in FIGS. 5A and 6A, first mode shape 64A can be formed by vibration of base plate 42 that causes a repeating pattern around the periphery of male taper portion 60, in this case a generally triangular shape with three vertices such as points 66A.

Figure 5B:
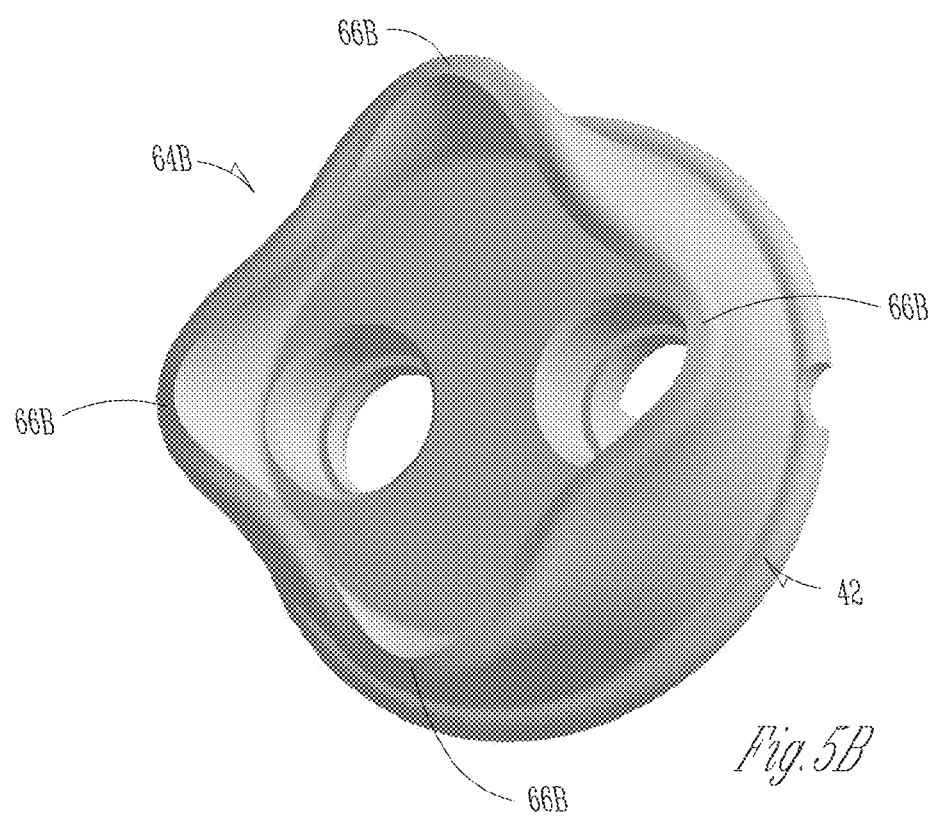
Figure 5C:
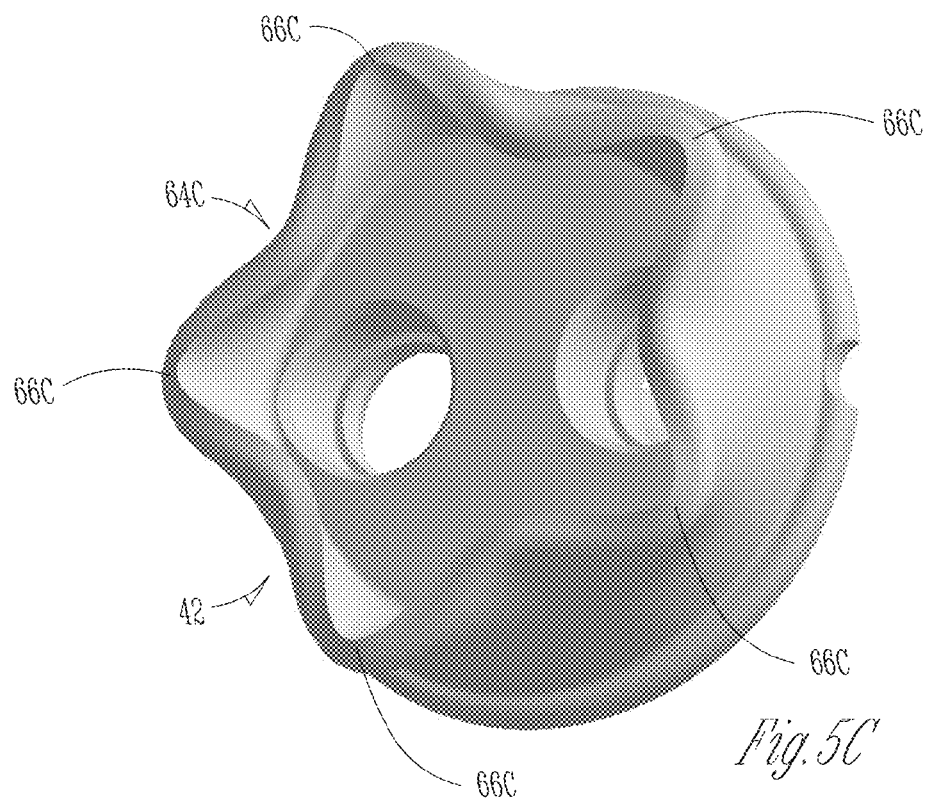
Figure 5D:
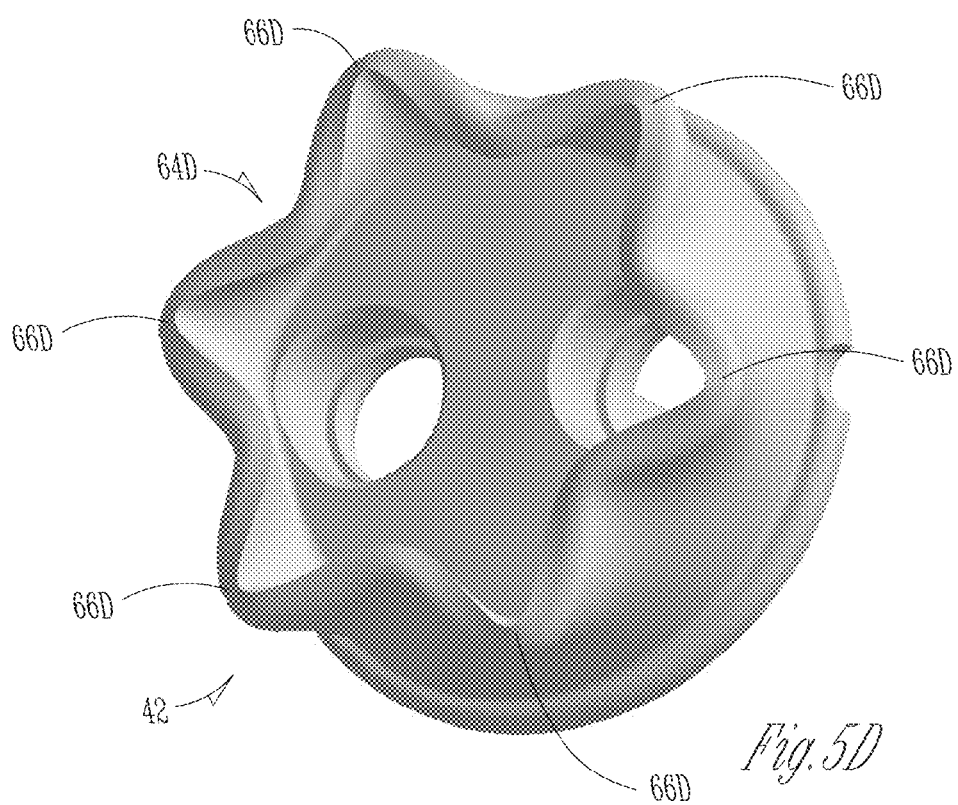

FIGS. 5B/6B, 5C/6C, and 5D/6D show base plate 42 in a second order mode, a third order mode, and fourth order mode, respectively. The second, third, and fourth order modes shown in FIGS. 5B-5D and 6B-6D correspond to the resonance frequency mode shapes 64B, 64C, 64D experienced by base plate 42 when exposed to a second ultrasonic vibration frequency that substantially matches a second natural frequency of vibration of base plate 42, a third ultrasonic vibration frequency that substantially matches a third natural frequency of vibration of base plate 42, and a fourth ultrasonic vibration frequency that substantially matches a fourth natural frequency of vibration of base plate 42, respectively. As shown in FIGS. 5B-5D and 6B-6D, second order shape 64B can comprise four vertices such as points 66B, third order shape 64C can comprise five vertices such as points 66C, and fourth order shape 64D can comprise six vertices such as points 66D.

Figure 7A:
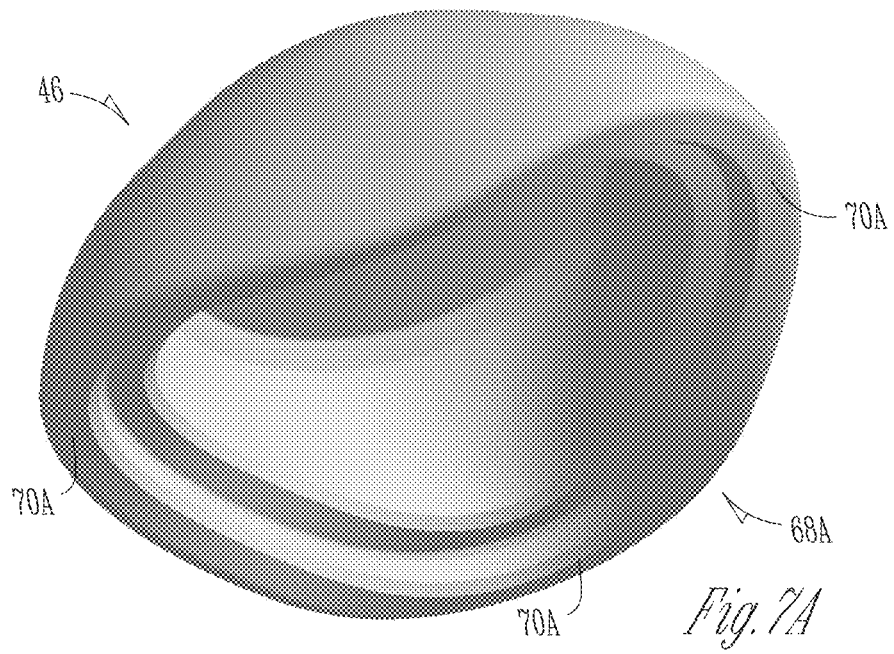
FIGS. 7A-7D are perspective views of examples of mode shapes at natural frequencies of vibration of the glenosphere of the artificial shoulder of FIG. 3 when the glenosphere is subjected to ultrasonic vibration configured to dissociate the taper connection between the base plate and the glenosphere.
Figure 8A:
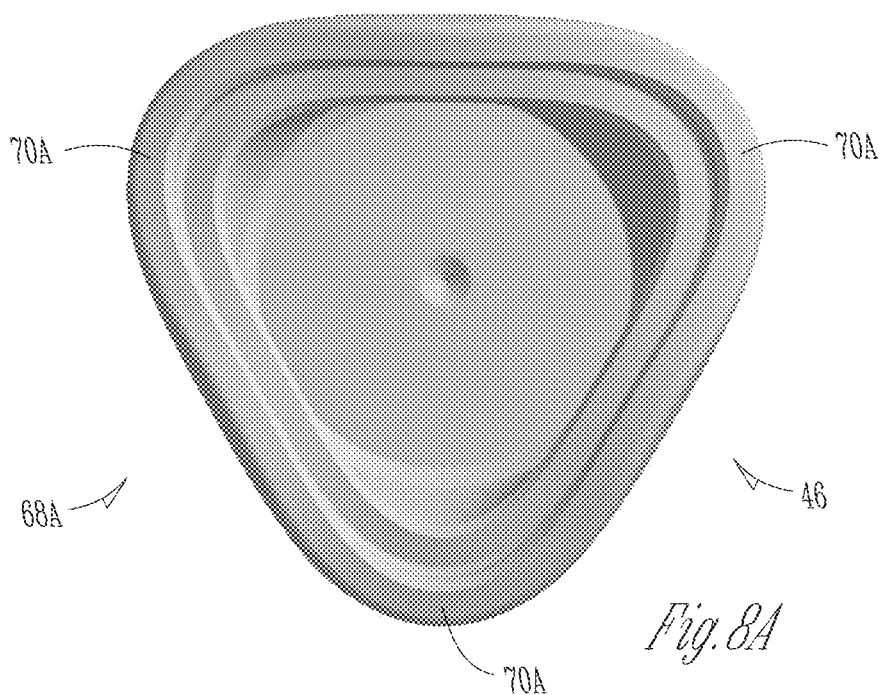
FIGS. 8A-8D are plan views of examples of the mode shapes at natural frequencies of vibration of the glenosphere shown in FIGS. 7A-7D.
Figure 8B:
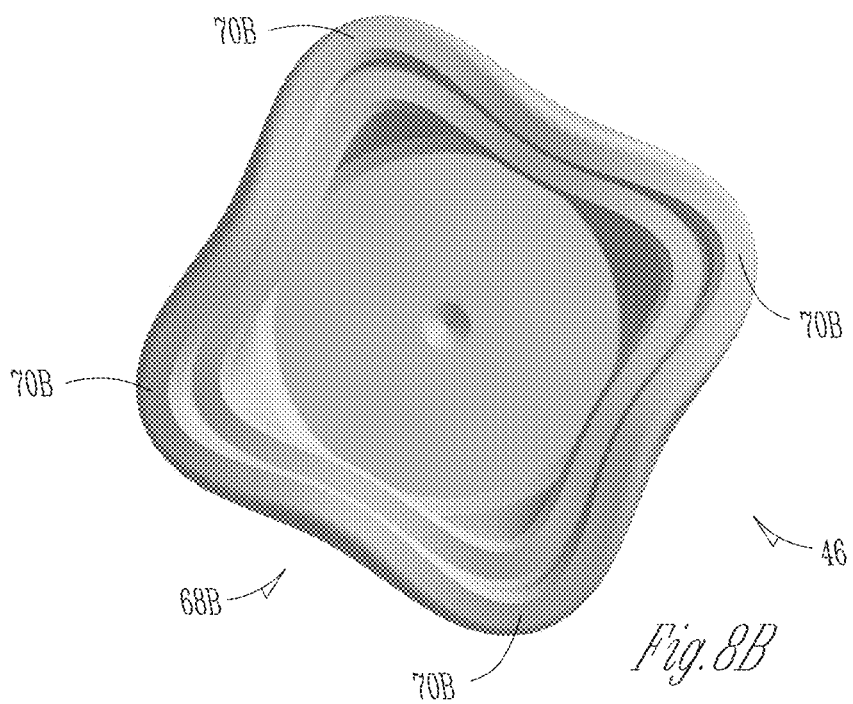
Figure 8C:
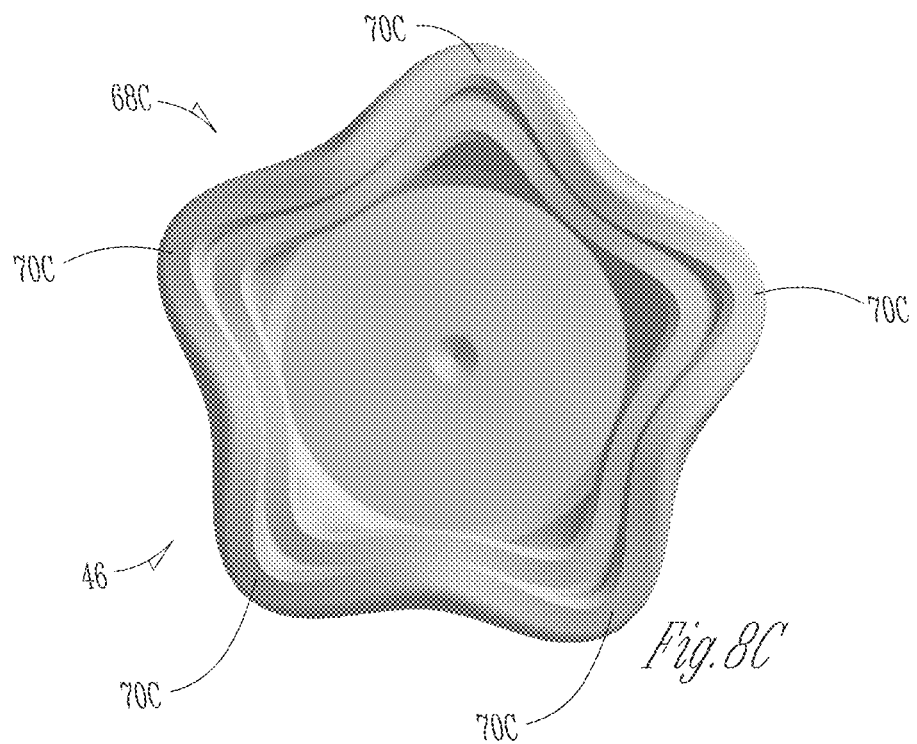
Figure 8D:
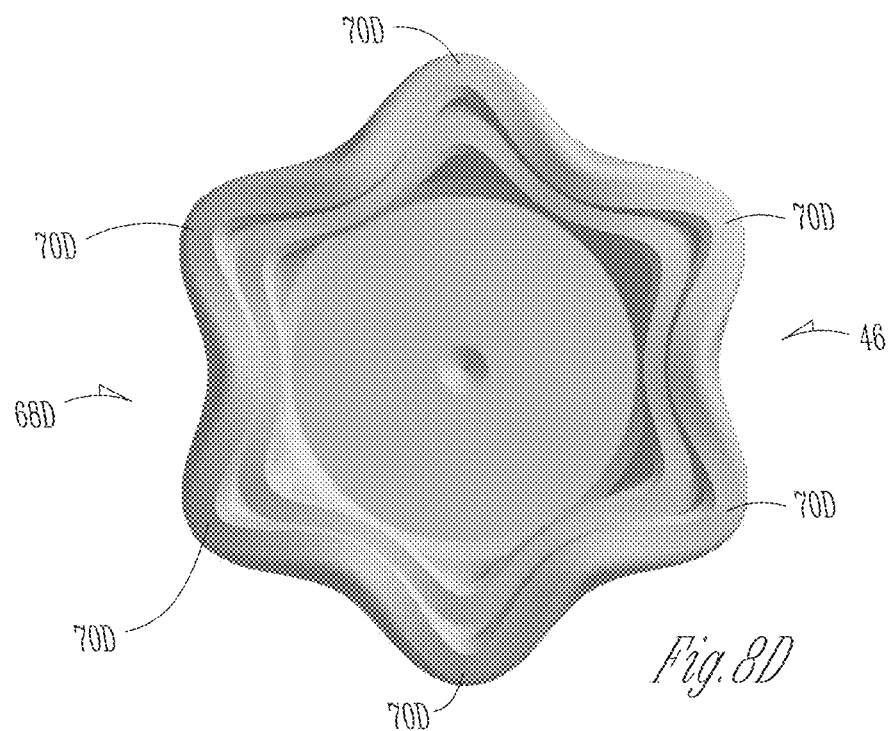

FIGS. 7A and 8A show glenosphere 46 within a first order mode while being exposed to a first frequency of ultrasonic vibration 32 that substantially matches a first natural frequency of vibration of glenosphere 46 such that glenosphere 46 comprises a first resonance frequency mode shape 68A. As shown in FIGS. 7A and 8A, first mode shape 68A can be formed by vibration of glenosphere 46 that causes a repeating pattern around the periphery of female taper portion 62, in this case a generally triangular shape with three vertices such as points 70A.

Figure 7B:
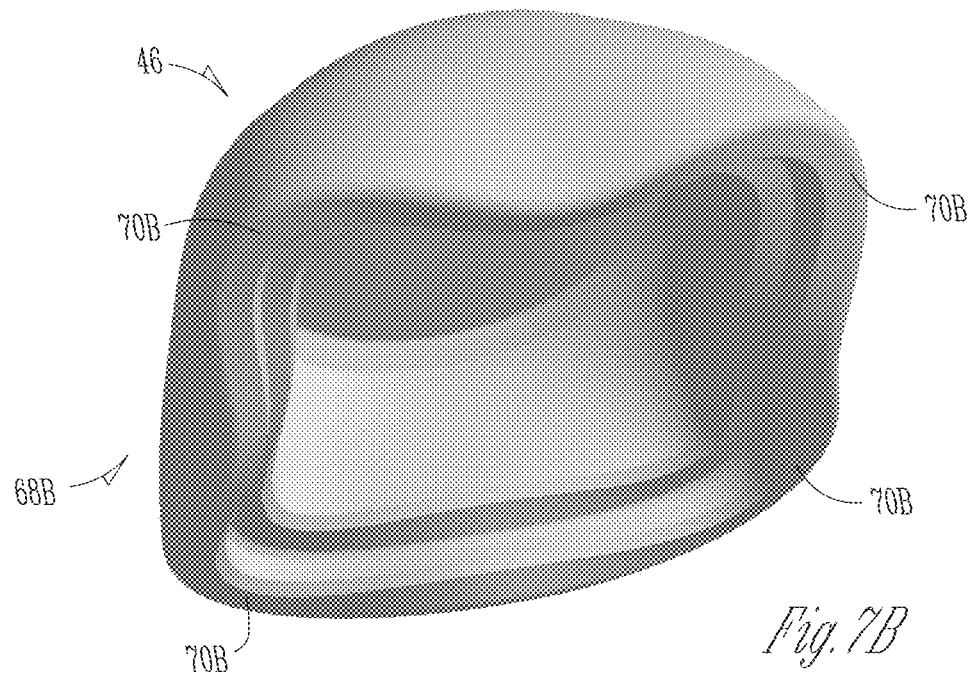
Figure 7C:
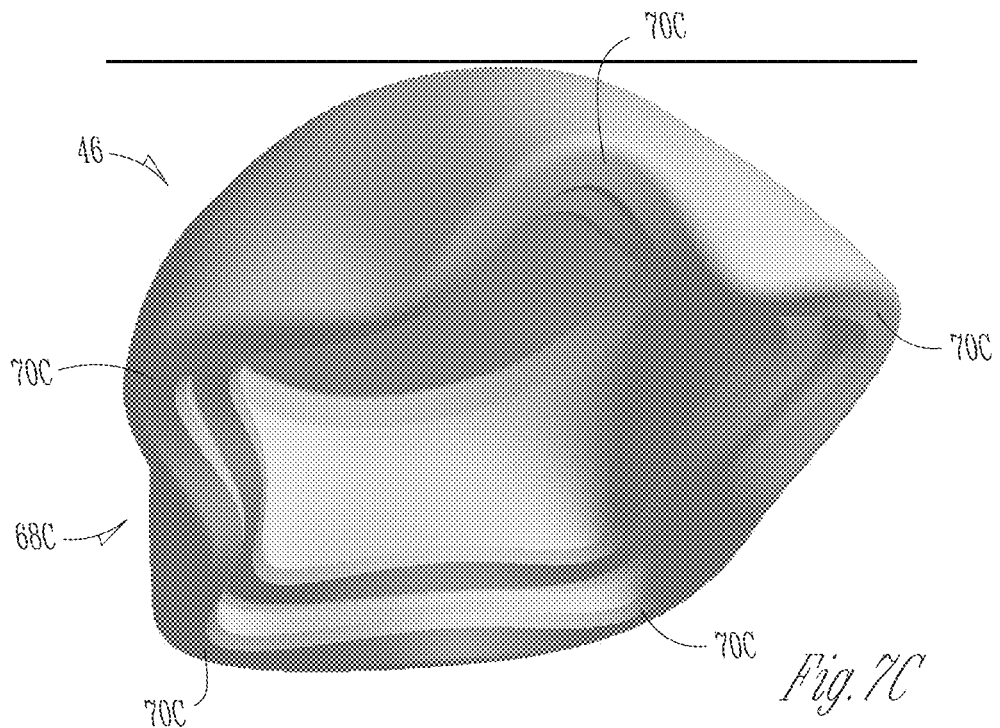
Figure 7D:
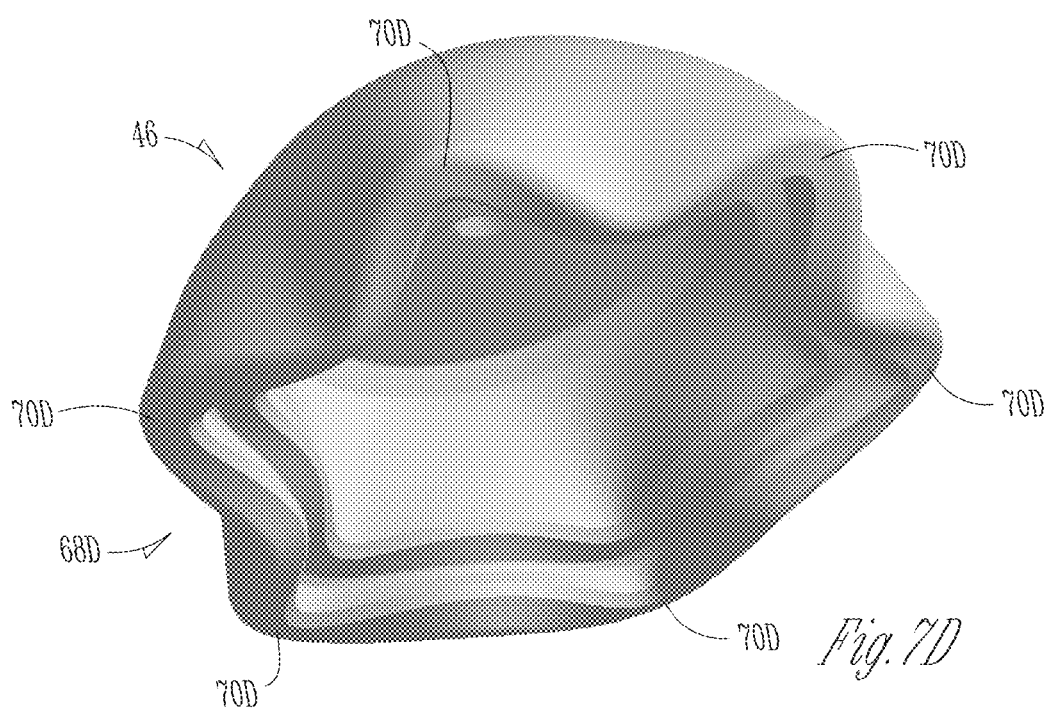

FIGS. 7B/8B, 7C/8C, and 7D/8D show glenosphere 46 in a second order mode, a third order mode, and fourth order mode, respectively. The second, third, and fourth order modes shown in FIGS. 7B-7D and 8B-8D correspond to the resonance frequency mode shapes 68B, 68C, 68D experienced by glenosphere 46 when exposed to a second ultrasonic vibration frequency that substantially matches a second natural frequency of vibration of glenosphere 46, a third ultrasonic vibration frequency that substantially matches a third natural frequency of vibration of glenosphere 46, and a fourth ultrasonic vibration frequency that substantially matches a fourth natural frequency of vibration of glenosphere 46, respectively. As shown in FIGS. 7B-7D and 8B-8D, second order shape 68B can comprise four vertices such as points 70B, third order shape 68C can comprise five vertices such as points 70C, and fourth order shape 68D can comprise six vertices such as points 70D.

Figure 9:
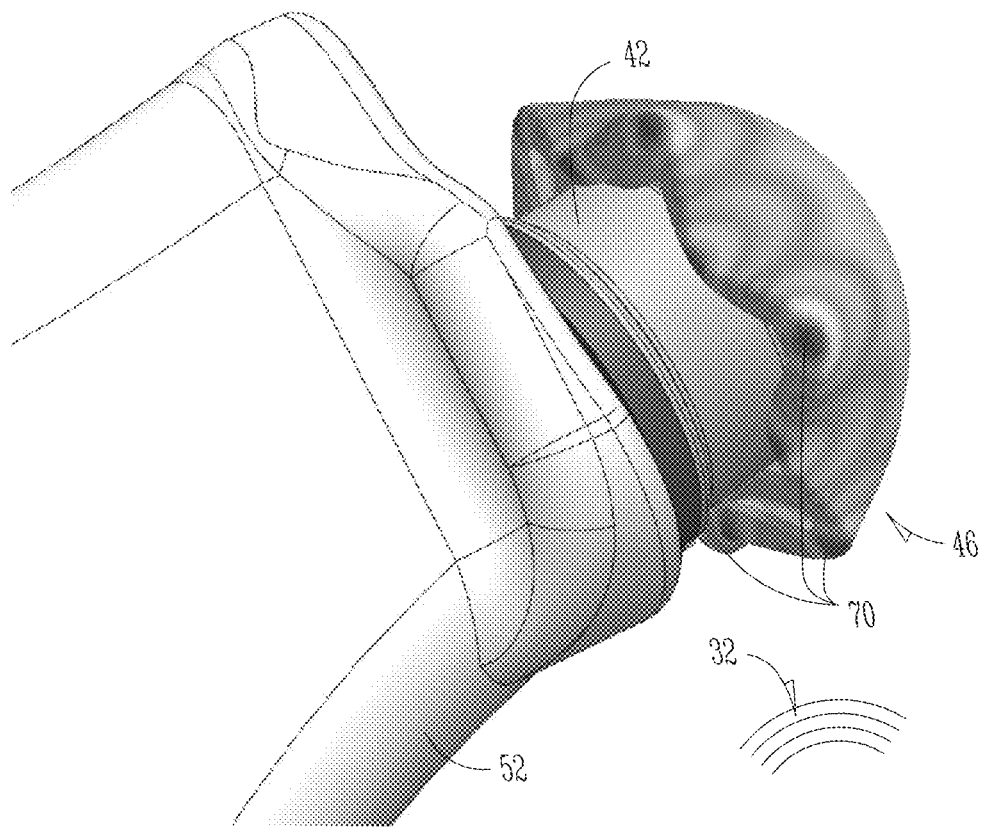
FIG. 9 is a conceptual view of an example of the base plate engaged with the glenosphere of the artificial shoulder of FIG. 3 with the glenosphere vibrating while being subjected to ultrasonic vibration at a natural frequency of vibration of the glenosphere in order to dissociate the glenosphere from the base plate.

FIG. 9 is a perspective view of base plate 42 and glenosphere 46, with base plate 42 attached to scapula 52. The remainder of artificial shoulder 40 (e.g., liner 48, stem 50, and, if present, spacer 58) is omitted for clarity. In the example shown in FIG. 9, ultrasonic vibration 32 has been applied to base plate 42 and glenosphere 46. In the example shown in FIG. 9, ultrasonic vibrations 32 are being applied at a frequency and amplitude that is sufficient to excite vibrations within glenosphere 46. In the example shown in FIG. 9, ultrasonic vibration 32 was applied at a frequency that substantially corresponds to a natural frequency of vibration of glenosphere 46 (for example, the frequency of ultrasonic vibration 32 is within about 1000 Hz from a natural frequency of vibration of glenosphere 46) such that glenosphere 46 forms a mode shape 68 (in this example, fourth order mode shape 68D described above with respect to FIGS. 7D and 8D). The vibration of glenosphere 46 that forms mode shape 68D allows the taper connection between male taper portion 60 of base plate 42 and female taper portion 62 of glenosphere 46 to be overcome so that glenosphere 46 can be dissociated from base plate 42.

Resonance vibrations within male taper portion 60 and/or female taper portion 62, such as the vibration of glenosphere 46 shown in the example of FIG. 9, are believed to interrupt the taper fit that had existed between male taper portion 60 and female taper portion 62 and allow for decoupling. After applying ultrasonic vibration 32 in order to achieve vibrations, glenosphere 46 can be separated and decoupled from base plate 42, for example in order to allow for removal of base plate 42 from scapula 52, to allow for repositioning of glenosphere 46 with respect to base plate 42, or to allow for replacement of one or both of base plate 42 and glenosphere 46.

As shown in the example of FIG. 9, ultrasonic vibration 32 can be applied such that only one component of the taper connection is excited to vibration, such as only glenosphere 46 being vibrated, as shown in FIG. 9. In this example, the frequency of ultrasonic vibration 32 does not correspond to a natural frequency of vibration of base plate 42 so that, as shown in FIG. 9, base plate 42 is not visibly vibrating, e.g., base plate 42 does not exhibit a resonance mode shape 64. In contrast, ultrasonic vibration 32 can be applied in such a way as to excite vibration in both components of the taper connection, e.g., in both base plate 42 and glenosphere 46 (not shown). The present disclosure is not limited to configurations that provide for vibration in only one component, e.g., in only male taper portion 60 of base plate 42 or only female taper portion 62 of glenosphere 46, or to configuration where multiple components, e.g., both male taper portion 60 of base plate 42 and female taper portion 62 of glenosphere 46. Rather, ultrasonic vibration 32 can be configured in any way that will provide for dissociation of male taper portion 60 and female taper portion 62. For example, ultrasonic vibration 32 can be configured to excite vibrations within glenosphere 46 while base plate 42 remains substantially unvibrated, as shown in the example of FIG. 9, ultrasonic vibration 32 can be configured to excite vibrations within base plate 42 while glenosphere 46 remains substantially un-vibrated (e.g., at rest) (not shown), or ultrasonic vibration 32 can be configured so that both base plate 42 and glenosphere 46 produce vibrations (not shown), such as by configuring ultrasonic vibration 32 with a frequency that is close enough to (e.g., within a predetermined or specified threshold) a natural frequency of vibration of both base plate 42 and glenosphere 46 or of a natural frequency of vibration of the combination assembly of base plate 42 and glenosphere 46, which may have a natural frequency of vibration that is the same as or different from a natural frequency of vibration of one or both of base plate 42 and glenosphere 46.

In order to apply an ultrasonic vibration 32 that will dissociate a taper coupling, the frequency or frequencies of ultrasonic vibration 32 that will dissociate the taper can be determined. In an example, such as described above, the frequency that will dissociate the taper can comprise a natural frequency of vibration of one of the components of the medical device comprising the taper, such as base plate 42 and/or glenosphere 46 of artificial shoulder 40. A general method of determining natural frequencies of vibration of a particular component or combination of components can comprise securing the component in a testing apparatus, setting an ultrasonic vibration producing device, such as decoupling device 32, to produce a range of frequencies, and analyzing the vibration response of the component in order to determine the natural frequency or frequencies of vibration of the component. Information determined from or about one or more natural frequencies of vibration of the component or components can then be stored, for example, as presets for controlling operation of a dissociation device 30, for example in memory 78 of dissociation device 30 (such as described below).

An example of the general method of determining one or more natural frequencies of vibration will be described more specifically with respect to artificial shoulder 40. In an example, natural frequencies of vibration for artificial shoulder 40 were determined using simulation software, such as ANSYS simulation analysis software from ANSYS, Inc. (Canonsburg, Pa., USA), for each component separately. Natural frequencies of vibration of each component could also be determined through experimental analysis of the component. The general method described above can be applied to base plate 42, to glenosphere 46, or to one or more other components of artificial shoulder 40, separate from one another. In another example of a method of determining the natural frequency of vibration, male taper portion 60 of base plate 42 was coupled with female taper portion 62 of glenosphere 46 in order to determine natural frequencies of vibration of base plate 42 combined with glenosphere 46 in the same manner as described above with respect to base plate 42 alone and glenosphere 46 alone.

Securing the component in a testing apparatus can comprise potting the component in a bone cement so as to simulate the structure to which the component may be secured. For example, base plate 42 can be potted in a first bone cement that can be configured to simulate scapula 52, and stem 50 can be potted in a second bone cement that can be configured to simulate humerus 54. In an example, such as described in more detail below, base plate 42 can be potted in bone cement and glenosphere 46 can be coupled with base plate 42 such as via male taper portion 60 and female taper portion 62.

Setting the frequency output of the ultrasonic vibration producing device, e.g., dissociation device 30, can comprise setting the device at a first frequency that is at or below a lowest expected natural frequency of vibration, followed by increasing the frequency output by the ultrasonic vibration producing device by selected increments (such as, for example, by 100 Hz, 250 Hz, 500 Hz, 1000 Hz, 2000 Hz, 5000 Hz or any other practical increment). After increasing the output frequency for each increment, the component can be tested to determine whether a natural frequency of vibration is achieved. In an example of determining one or more natural frequencies of vibration, the frequency that is output by dissociation device 30 can be continuously increased from the lowest range of ultrasonic frequencies until a first natural frequency of vibration is experienced by the component or components being tested and the dissociation device 30 can continue to continuously increase the output frequency until one or more subsequent natural frequencies of vibration are achieved.

Analysis of the vibration response of the component being tested may be performed by a spectrum analyzer, which can include software and/or hardware. For example, such spectrum analyzer can be used to determine whether base plate 42 is experiencing a natural frequency of vibration (e.g., displaying a mode shape 64 as described above). For example, one or more accelerometers can be placed on base plate 42 to measure vibrations produced such as when a natural mode of frequency is achieved. In an example, vibration data can be acquired by a high frequency microphone that is capable of capturing the "sound" or ultrahigh frequencies experienced by base plate 42.

The vibration data may be fed into software that is capable of analyzing the vibration data and determining the frequency at which the component vibrates and/or indicate when a resonant mode shape is reached. In an example, the software can be configured to be capable of performing Fast Fourier Transform (FFT) analysis and can be configured to extract the one or more natural frequencies of vibration from the vibration data captured.

Results of an example of natural frequency of vibration simulation analysis of base plate 42 are shown in Table 1.

TABLE 1

Example of Natural Frequencies of Vibration of a Base Plate from a Reverse Shoulder Implant

| Mode # | Frequency (Hz) | Frequency (MHz) |
| --- | --- | --- |
| 1 | 16,850 | 0.016850 |
| 2 | 54,657 | 0.054657 |
| 3 | 54,657 | 0.054657 |
| 4 | 54,999 | 0.054999 |
| 5 | 55,353 | 0.055353 |
| 6 | 55,735 | 0.055735 |
| 7 | 58,941 | 0.058941 |
| 8 | 63,828 | 0.063828 |
| 9 | 63,944 | 0.063944 |
| 10 | 66,259 | 0.066259 |
| 11 | 66,259 | 0.066259 |
| 12 | 78,505 | 0.078505 |
| 13 | 80,921 | 0.080921 |
| 14 | 80,921 | 0.080921 |
| 15 | 81,248 | 0.081248 |
| 16 | 83,518 | 0.083518 |
| 17 | 83,559 | 0.083559 |
| 18 | 91,459 | 0.091459 |
| 19 | 106,000 | 0.106000 |
| 20 | 106,020 | 0.106020 |
| 21 | 114,970 | 0.114970 |
| 22 | 114,970 | 0.114970 |
| 23 | 127,670 | 0.127670 |
| 24 | 127,670 | 0.127670 |
| 25 | 130,110 | 0.130110 |
| 26 | 131,350 | 0.131350 |

TABLE 1-continued

Example of Natural Frequencies of Vibration of a Base Plate from a Reverse Shoulder Implant

| Mode # | Frequency (Hz) | Frequency (MHz) |
|---|---|---|
| 27 | 131,350 | 0.131350 |
| 28 | 132,210 | 0.132210 |
| 29 | 132,720 | 0.132720 |
| 30 | 141,800 | 0.141800 |

Each frequency mode listed in Table 1 resulted in some form of vibration within base plate 42. However, the modes corresponding to natural frequencies of vibration, e.g., those that correspond to mode shapes 64A-64D in FIGS. 5A-5D and 6A-6D, were mode number 3 (54,657 Hz, corresponding to mode shape 64A in FIGS. 5A and 6A), mode number 6 (55,735 Hz, corresponding to mode shape 64B in FIGS. 5B and 6B), mode number 11 (66,259 Hz, corresponding to mode shape 64C in FIGS. 5C and 6C), mode number 16 (83,518 Hz, corresponding to mode shape 64D in FIGS. 5D and 6D), mode number 19 (106,000 Hz, not shown), and mode number 29 (132,720 Hz, not shown).

Results of a natural frequency of vibration simulation analysis of glenosphere 46 are shown in Table 2.

TABLE 2

Example of Natural Frequencies of Vibration of a Glenosphere from a Reverse Shoulder Implant

| Mode # | Frequency (Hz) | Frequency (MHz) |
|---|---|---|
| 1 | 2,089,100 | 2.0891 |
| 2 | 2,090,200 | 2.0902 |
| 3 | 2,496,900 | 2.4969 |
| 4 | 2,497,000 | 2.4970 |
| 5 | 3,345,400 | 3.3454 |
| 6 | 3,345,900 | 3.3459 |
| 7 | 4,292,200 | 4.2922 |
| 8 | 4,339,700 | 4.3397 |
| 9 | 4,813,100 | 4.8131 |
| 10 | 5,395,500 | 5.3955 |
| 11 | 5,369,500 | 5.3695 |
| 12 | 6,472,200 | 6.4722 |
| 13 | 6,473,100 | 6.4731 |
| 14 | 7,014,900 | 7.0149 |
| 15 | 7,080,700 | 7.0807 |
| 16 | 7,082,100 | 7.0821 |
| 17 | 7,760,000 | 7.7600 |
| 18 | 7,760,200 | 7.7602 |
| 19 | 7,770,500 | 7.7705 |
| 20 | 7,772,900 | 7.7729 |
| 21 | 8,151,100 | 8.1511 |
| 22 | 8,154,500 | 8.1545 |
| 23 | 9,460,400 | 9.4604 |
| 24 | 9,465,500 | 9.4655 |
| 25 | 9,556,200 | 9.5562 |
| 26 | 9,556,800 | 9.5568 |
| 27 | 9,784,900 | 9.7849 |
| 28 | 9,788,600 | 9.7886 |
| 29 | 10,233,000 | 10.233 |
| 30 | 20,891,000 | 20.891 |

Each frequency mode listed in Table 2 resulted in some form of vibration within glenosphere 46. However, in an example, the desired mode shapes, such as those corresponding to natural frequencies of vibration, e.g., those that correspond to mode shapes 68A-68D in FIGS. 7A-7D and 8A-8D, were mode number 1 (2.0891 MHz, not shown), mode number 5 (3.3454 MHz, corresponding to mode shape 68A in FIGS. 7A and 8A), mode number 10 (5.3965 MHz, corresponding to mode shape 68B in FIGS. 7B and 8B), mode number 17 (7.76 MHz, corresponding to mode shape 68C in FIGS. 7C and 8C), and mode number 30 (20.891 MHz, corresponding to mode shape 68D in FIGS. 7D and 8D).

A natural frequency analysis of base plate 42 and glenosphere 46 combined, e.g., with male taper portion 60 inserted into and engaged with female taper portion 62, can be performed in the same way as the individual analysis of base plate 42 and glenosphere 46 described above. In an example, any of these natural frequencies of vibration of base plate 42, glenosphere 46, or the combination of base plate 42 and glenosphere 46, can be sufficient to dissociate male taper portion 60 from female taper portion 62. In an example, only certain natural frequencies of vibration may be capable of dissociating male taper portion 60 from female taper portion 62, wherein the certain natural frequencies of vibration may be those of only base plate 42, only those of glenosphere 46, only those of the combination of base plate 42 and glenosphere 46, or only certain ones of the plurality of natural frequencies of vibration of two or more of base plate 42, glenosphere 46, and the combination of base plate 42 and glenosphere 46. In an example, the frequency that is capable of dissociating male taper portion 60 from female taper portion 62 may be some other frequency, such as a natural frequency of vibration of the entire artificial shoulder 40 implanted within patient 1, or some other frequency.

In an example, a frequency that is capable of dissociating male taper portion 60 from female taper portion 62 can be or can include a natural frequency of vibration of base plate 42 individually, e.g., one of the natural frequencies of vibration for base plate 42 listed in Table 1, a natural frequency of vibration of glenosphere 46, e.g., one of the natural frequencies of vibration for glenosphere 46 listed in Table 2, or a natural frequency of vibration of the combination of base plate 42 and glenosphere 46.

Figure 10:
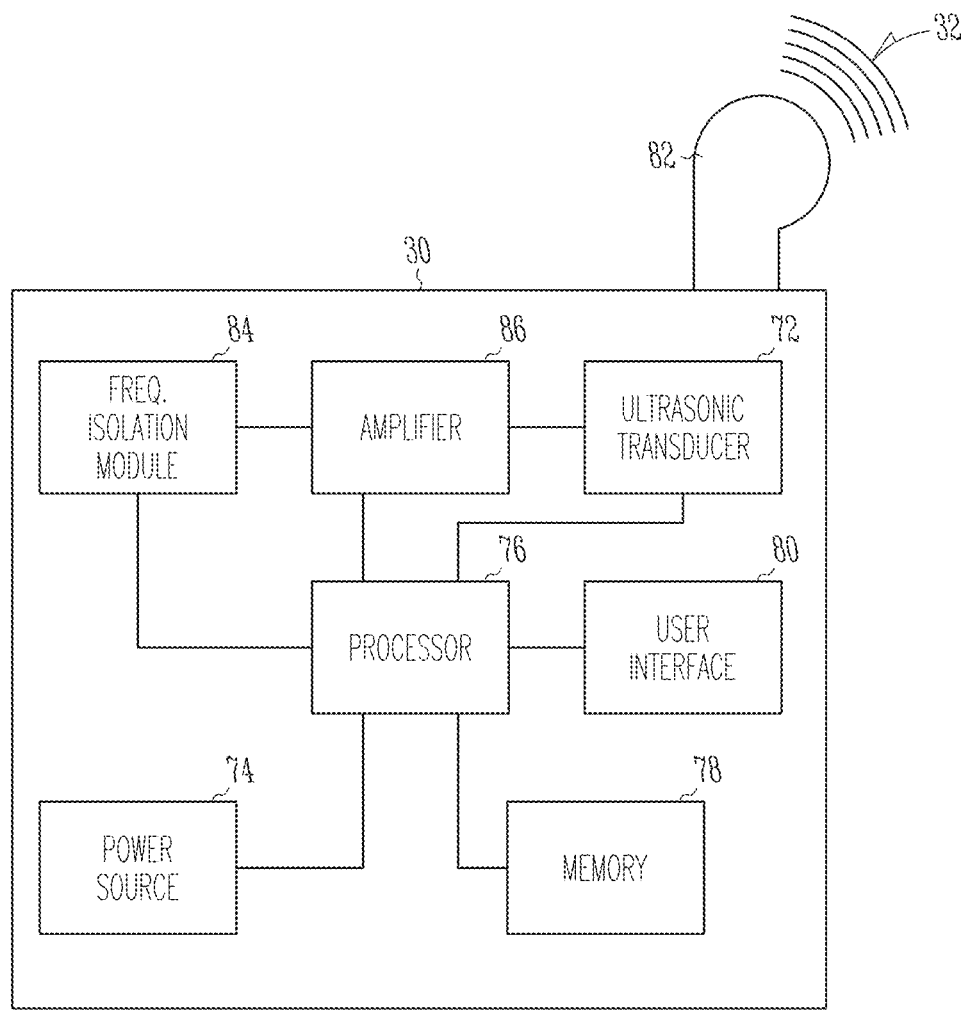
FIG. 10 is a schematic diagram of an example of a decoupling device capable of supplying ultrasonic vibration configured to dissociate the male taper portion from the female taper portion of a medical device.

FIG. 10 is a schematic diagram of an example dissociation device 30 capable of applying ultrasonic vibration 32 to a medical device, such as medical device 12 shown in FIGS. 1 and 2, or artificial shoulder 40 shown in FIGS. 3 and 4. In the example shown in FIG. 10, dissociation device 30 can comprise an acoustic transducer, such as an ultrasonic transducer 72, that can produce ultrasonic or other acoustic vibrations 32, a power source 74, such as a battery or a connection to alternating current power, a processor 76 or other circuit configured for controlling ultrasonic transducer 72, such as by controlling the frequency or amplitude of ultrasonic vibration 32, a memory 78 configured for storing instructions or other parameters used by processor 76, and a user interface 80, such as including a controller to allow a user, such as a physician or other medical professional, to control ultrasonic transducer 72. Dissociation device 30 can also comprise a director, such as an acoustic lense 82, configured for directing ultrasonic vibration 32 so that a user can direct ultrasonic vibration 32 toward a medical device 12, such as in particular toward the taper connection formed between male tapered portion 18 and female tapered portion 20. In an example, shown in FIG. 10, dissociation device 30 can also comprise a frequency isolation module 84, which can include a filter circuit that can be configured for filtering the desired frequency of ultrasonic drive signal while filtering out other high-frequency noise, and an amplifier 86 for enhancing the ultrasonic signal before transmitting ultrasonic vibrations 32 from ultrasonic transducer 72.

Ultrasonic transducer 72 converts energy, such as electrical energy from power source 72, to ultrasonic vibration 32. In an example, ultrasonic transducer 72 comprises a piezoelectric transducer that can be configured to convert an electrical signal, such as an electrical signal produced or controlled by processor 76, into acoustic pressure waves that are transmitted as ultrasonic vibration 32. In an example, ultrasonic transducer 72 and transmission device 73 can be configured to supply ultrasonic vibration 32 in one or more frequencies within the range of frequencies that can dissociate male taper portion 18 from female taper portion 20. Ultrasonic transducer 72 and transmission device 73, and, if included, frequency isolation module 84 and amplifier 86, may also be configured to supply ultrasonic vibration 32 with sufficient amplitude such that ultrasonic vibration 32 will have sufficient energy to dissociate male taper portion 18 from female taper portion 20. In an example, ultrasonic transducer 72 and (if present) frequency isolation module 84 and amplifier 86 can be configured to supply one or more frequencies of ultrasonic vibration 32 within a frequency range that extends from about 0.02 megahertz (MHz) to about 100 MHz, for example from about 0.5 MHz to about 50 MHz, such as from about 1 MHz to about 25 MHz. Further examples of frequencies of ultrasonic vibration 32 that dissociation device 30 can be configured to provide are described above, such as with respect to the natural frequencies of vibration of base plate 42 and glenosphere 46.

Ultrasonic transducer 72 can also be configured to supply ultrasonic vibration 32 having an amplitude that is sufficient to dissociate taper 10, but not so high that it raises the temperature of medical device 12, any of its components, any tissue surrounding medical device 12, or any intervening tissue between ultrasonic transducer 72 and medical device 12, beyond a desired temperature threshold. For an implantable prosthetic, such as artificial shoulder 40 described above as an example, it can be desirable to keep an increase in temperature of medical device, and thus the tissue of the patient, to less than a threshold value, such as about 2° C., above a nominal body temperature.

Processor 76 can be included in dissociation device 30 such as to control ultrasonic transducer 72, e.g., by controlling the electrical energy supplied to ultrasonic transducer 72 from power source 74. Processor 76 can execute instructions stored on an onboard or separate memory 78. Processor 76 can comprise a microprocessor, a controller, a digital signal processor (DSP), an application specific integrated circuit (ASIC), a field-programmable gate array (FPGA), or any other equivalent integrated or discreet logic circuitry, or any combination of such components. Memory 78 can include any volatile, non-volatile, magnetic, optical, or electrical storage medium, such as a random access memory (RAM), read-only memory (ROM), non-volatile RAM (NVRAM), magnetic RAM (MRAM), electrically-erasable programmable ROM (EEPROM), flash memory, or the like.

User interface 80 can comprise a controlling device that can allow a user to manually control the output of dissociation device 30, such as by controlling the output of ultrasonic transducer 72. User interface 80 can comprise any configuration capable of permitting a user, such as a surgeon or other clinician or health care practitioner, to input information or control processor 76 in order to control operation of dissociation device 30. Examples of user interface 80 include a touch screen device, physical controls such as knobs or buttons, or a computer input device configured to control dissociation device 30, such as a general computing device, e.g., a personal computer or mobile device, configured to interface with dissociation device 30, either directly or indirectly, such as through a network.

In an example, data about one or more medical devices 12 can be stored, for example in memory 78 of dissociation device 30 or within a memory of a general computing device configured to interface with dissociation device 30. Among other things, the data for a particular medical device 12 can comprise information regarding frequencies that are observed or expected to dissociate at least one taper 10 of medical device 12. For example, data corresponding to artificial shoulder 40 can comprise data regarding one or more natural modes of vibration of at least one of base plate 42, glenosphere 46, male taper portion 60, female taper portion 62, or for the entirety of artificial shoulder 40 such that an ultrasonic vibration 32 frequency within a predetermined or specified threshold of one of the natural frequencies of vibration can be selected. The data can also include one or more specific frequency profiles or programs that can be applied to a particular medical device 12, so that a specified protocol can be applied to medical device 12 such as in a particular order. The storage of data allows a user to simply select the specific type of medical device 12 and, if necessary, the taper 10 within medical device 12 that is desired to be dissociated. Processor 76 can use the data to control ultrasonic transducer 72 in a predetermined or specified way so that the user, such as a surgeon, can focus on physically dissociating the taper and need not worry about the frequency or amplitude of ultrasonic vibrations 32 applied to medical device 12.

The use of ultrasonic vibration 32 to effect taper dissociation provides for advantages over other methods of taper dissociation, which typically relied solely on relatively large impact, tensile, or rotational forces in an attempt to physically force the male taper portion from the female taper portion. The application of ultrasonic vibration 32 instead of or in addition to physical impact, tensile, or rotational forces imparts reduced physical force, or even little or no physical force, onto the medical device or onto the patient. In an example, the dissociation device 30 can be configured to apply ultrasonic vibration 32 to the medical device without even coming into contact with the medical device, or with only light contact between dissociation device 30 and the medical device. Rather, dissociation device 30 may be configured to supply ultrasonic vibration 30 with sufficient energy to travel a distance through a patient's tissue from dissociation device 30 to the taper of the medical device and still have sufficient energy to dissociate the male taper portion from the female taper portion.

In an example, dissociation device 30 can be configured such that ultrasonic vibration 32 can reach and dissociate the taper through the patient's body such as to effect dissociation of the taper even after implantation of the medical device is complete. For example, if after the surgery to implant artificial shoulder 40 is complete and the patient 1 has been using it for an extended period of time it is discovered that one or more components of artificial shoulder 40 are not properly aligned, it can be possible to apply ultrasonic vibration 32 through patient 1 to artificial shoulder 40, dissociate male taper portion 60 from female taper portion 62, properly align the components of artificial shoulder 40, and reengage male taper portion 60 and female taper portion 62 without having to perform a follow-up surgery on patient 1. In an example, alignment of the components and reengaging of the taper can be achieved by manipulating the arm and shoulder of patient 1 in order to achieve proper alignment and then to force male taper portion 60 back into female taper portion 62. Eliminating the follow-up surgery advantageously reduces the likelihood of complications that can arise during surgery, such as surgeon error or infection.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A method comprising:
   providing or obtaining access to a medical device comprising a first component comprising a male portion and a second component comprising a corresponding female portion engaged with the male portion; and
   applying acoustic vibration to the medical device,
   wherein the acoustic vibration is configured to dissociate the male portion from the female portion.

2. The method of claim 1, wherein the acoustic vibration comprises ultrasonic vibration.

3. The method of claim 1, wherein the male portion comprises a male taper and the female portion comprises a corresponding female taper.

4. The method of claim 1, further comprising, before applying the acoustic vibration, selecting a frequency for the acoustic vibration that is sufficient to dissociate the male portion from the female portion.

5. The method of claim 4, wherein the selected frequency of the acoustic vibration is within a predetermined or specified threshold of a natural frequency of vibration of at least one of the medical device, the first component, the second component, the male portion, or the female portion.

6. The method of claim 5, wherein the predetermined or specified threshold is within about 1000 Hz from the natural frequency of vibration.

7. The method of claim 5, wherein the predetermined or specified threshold is within about 5% of the natural frequency of vibration.

8. The method of claim 1, wherein the medical device comprises one of an artificial shoulder implant, an artificial hip implant, an artificial elbow implant, an artificial knee, an artificial ankle implant, an artificial wrist implant, a dental implant, or a spinal implant.

9. The method of claim 1, comprising separating the male taper portion from the acoustically-dissociated female taper portion.

10. A dissociation device comprising: an ultrasonic transducer configured to produce ultrasonic vibration selected to be sufficient to dissociate a male taper portion from an engaged corresponding female taper portion of a medical device, wherein a first component of the medical device comprises the male taper portion and a second component of the medical device comprises the female taper portion;
   wherein the transducer is configured to produce the ultrasonic vibration with a frequency that is within a predetermined or specified threshold of a natural frequency of vibration of at least one of the medical device, the first component, the second component, the male taper portion, or the female taper portion;
   a processor configured to control the ultrasonic transducer;
   a memory, wherein the memory stores at least one of the natural frequency of vibration of at least one of the male taper portion and the female taper portion, the predetermined or specified threshold, and one or more instructions for the processor; and
   a user interface configured to allow a user to select a frequency for the ultrasonic vibration.

11. The dissociation device of claim 10, wherein the transducer is configured so that the predetermined or specified threshold is within about 1000 Hz from the natural frequency of vibration.

12. The dissociation device of claim 10, wherein the transducer is configured so that the predetermined or specified threshold is within about 5% of the natural frequency of vibration.

13. The dissociation device of claim 10, wherein the memory is configured to store a plurality of specific frequency profile protocols for a plurality of medical devices, the plurality of specific frequency profile protocols including a set of instructions for applying a plurality of frequencies in a predefined order, each specific frequency profile protocol corresponding to one medical device of the plurality of medical devices.

14. A method, comprising:
providing or obtaining access to a medical device including a first component having a male taper portion and a second component having a corresponding female taper portion engaged with the male portion;
selecting a frequency for an acoustic vibration that is sufficient to dissociate the male portion from the female portion, wherein the selected frequency of the acoustic vibration is within a predetermined or specified threshold of a natural frequency of vibration of at least one of the medical device, the first component, the second component, the male portion, and the female portion; and
applying the acoustic vibration to at least one of the medical device, the first component, the second component, the male portion, and the female portion, wherein the acoustic vibration dissociates the male portion from the female portion.

15. The method of claim 14, wherein selecting the frequency includes selecting a frequency via a user interface of a dissociation device configured to apply the acoustic vibration.

16. The method of claim 14, wherein the acoustic vibration comprises ultrasonic vibration.

17. The method of claim 14, wherein selecting the frequency for the acoustic vibration that is sufficient to dissociate the male portion from the female portion includes selecting a specific frequency profile protocol that includes a plurality of frequencies that are to be applied in a predefined order to at least one of the medical device, the first component, the second component, the male portion, and the female portion.

18. The method of claim 14, wherein the predetermined or specified threshold is within about 5000 Hz from the natural frequency of vibration.

19. The method of claim 14, wherein the transducer is configured so that the predetermined or specified threshold is within about 10% of the natural frequency of vibration.

* * * * *